United States Patent [19]
Field

[11] 3,992,766
[45] Nov. 23, 1976

[54] APPARATUS FOR PROCESSING ELASTIC ARTICLES
[75] Inventor: Donald G. Field, Lawrenceville, N.J.
[73] Assignee: Youngs Rubber Corporation, Trenton, N.J.
[22] Filed: Aug. 26, 1975
[21] Appl. No.: 607,936

[52] U.S. Cl. .............................. 29/235; 214/1 BC; 214/1 BE; 214/1 BH; 214/1 BV
[51] Int. Cl.² .................. B23P 19/00; B65G 47/04; B23P 11/02
[58] Field of Search .......... 29/200 A, 200 D, 200 P, 29/208 R, 234, 235, 407, 450; 214/1 BC, 1 BA, 1 BE, 1 BH, 1 BS, 1 BV

[56] References Cited
UNITED STATES PATENTS

| | | | |
|---|---|---|---|
| 3,253,719 | 5/1966 | Povlacs et al. | 214/1 BV |
| 3,588,997 | 6/1971 | Field | 29/450 |
| 3,820,666 | 6/1974 | Nye et al. | 214/1 BV |

Primary Examiner—C.W. Lanham
Assistant Examiner—E. M. Combs
Attorney, Agent, or Firm—Arthur B. Colvin

[57] ABSTRACT

The present invention is directed to improvements in the method and apparatus for processing elastic articles, such as condoms. The invention is directed more specifically to an automated apparatus which is effective, to select single condoms or like articles from a bulk storage area to which they are delivered after manufacture, the articles being typically partially or entirely covered with a powdered lubricant, such as talc; advancing the articles to a mounting station, the articles being substantially cleaned of talc in the course of such advancing movement; the articles being thereafter automatically fed to an apparatus which distends the articles in such manner that the same may be mounted on test mandrels of a diameter larger than the diameter of the distended condoms.

9 Claims, 20 Drawing Figures

APPARATUS FOR PROCESSING ELASTIC ARTICLES

This invention relates more particularly to an apparatus and method for processing condoms or the like such that the same may be fed to a mounting apparatus, as more particularly shown in U.S. Pat. No. 3,588,997.

BACKGROUND OF THE INVENTION

1. Field of the Invention

The present invention is in the field of processing elastic articles, and particularly a method and apparatus for processing elastic articles such as condoms.

2. The Prior Art

In the manufacture of elastic articles such as condoms, finger cots and like stretchable commodities, it is obviously necessary to assure that the same are impervious to the passage of fluid. Numerous processes have been developed for the testing of the finished articles.

In accordance with a preferred method, a conductive mandrel is covered by an article which is mounted thereon, the dimensions of the mandrel being larger than the comparable dimensions of the undistended articles. Testing of the article mounted on the mandrel is thereafter effected by dipping the covered mandrel into a conductive solution, electrical apparatus being employed to check against leaks. Obviously, failure of the cover to insulate the mandrel completely, signifies leakage in the condom and the same must be discarded as defective.

Typically, in the course of manufacture and prior to testing, finished condoms are partially covered on their surfaces with a powered lubricant, such as talc, in order to prevent the articles from sticking together by engagement of raw latex surfaces upon subsequent rolling.

Testing procedures have heretofore been effected by operators manually stretching the unrolled condoms onto advancing mandrels of the testing apparatus. The operation of physically mounting the articles on mandrels has been found to represent a high percentage of the cost of the total manufacturing process. Additionally, a high percentage of defective products have been found to have been incurred in the course of manually mounting the same on mandrels.

Additionally, removal of the talc, which is preferably accomplished prior to testing, has not be effectively done in the course of manual mounting.

In U.S. Pats. Nos. 3,588,997 and 3,253,719, means have been suggested for automating the theretofore manually effected operations.

The present invention is directed to further improvements in the mounting operation and particularly improvements on the apparatus and method described in U.S. Pat. No. 3,588,977

SUMMARY

The present invention may be summarized as directed to improvements in the method and apparatus for mounting condoms and like elastic articles on mandrels, the sizing of the mandrels and articles being such that the articles are distended in the mounted position.

More particularly, in accordance with the apparatus phases thereof, the invention relates to mechanism for selecting single articles from a bulk supply, the articles being in unrolled condition, and typically partially coated or covered with a dry powdered lubricant, such as talc, feeding the articles from a pickup station by means of a conveyor apparatus which orients the articles and clears the dry powdered lubricant from both the outer and inner surfaces thereof.

In the apparatus and method of the invention, the articles are mounted on carrier mandrels of lesser diameter than the diameter of the articles, the carrier mandrels being mounted on a conveyer mechanism which serially deposits the articles into vacuum chamber apparatus which distends the articles by means of reducing the pressure externally of the articles to subatmospheric levels, whereby atmospheric pressure within the articles causes the same to stretch to a degree which would permit the insertion thereinto of the test mandrels.

The invention is characterized by a plurality of improvements resulting in a more efficient and effective manufacturing apparatus and method. Inter alia the unrolled articles are fed through a conduit or tube incorporating barriers which effectively orient the articles, the barriers being accompanied by vaccum stations which clean excess talc or dry lubricant from the external surfaces of the advancing articles. The articles are then rapidly impacted, closed end first, against the carrier mandrels, the momentum of the articles being sufficient to evert the articles, e.g., turn the same inside out, exposing the surface of the articles which was innermost in the course of movement along the conduit. The now exposed surface of the everted articles is subjected to further cleaning influences, effective to remove the talc therefrom.

Mechanism is provided for maintaining the articles on the carrier mandrels and releasing the same to the vacuum distending chambers previously briefly described and described in detail in U.S. Pat. No. 3,588,997,.

The invention further relates to a method for feeding orienting and cleaning both the interior and the exterior surfaces of condoms or like articles by advancing the same in a stream of moving air which will also serve to force the articles through restricting baffles functioning to orient the articles and dislodge powdered lubricant from the exposed surface, and thereafter impacting the rapidly advancing articles, closed end first, against the carrier mandrels which evert the articles, exposing the theretofore interior surface, and permitting the same to be subjected to cleaning influences to remove remaining amounts of talc or lubricant.

Accordingly, it is an object of the invention to provide an improved method and apparatus for the processing of distensible elastic articles, such as condoms.

It is a further object of the invention to provide an improved apparatus and method for mounting condoms, finger cots or the like on test mandrels of larger diameter than the diameter of the condoms.

Still a further object of the invention is the provision in the combination described of an improved novel vacuum conduit means which functions to orient, cleanse and advance condoms, one at a time, from a bulk supply to an intermediate conveyer, the apparatus being effective also to remove excessive talc from both the interior and the exterior surfaces of the articles.

Still a further object of the invention is the provision of apparatus of the type described and incorporating novel singulating means to assure that only a single article at a time may be fed to the conduit. To attain these objects and such further objects as may appear herein or be hereinafter pointed out, reference is made to the accompanying drawings, forming a part hereof, in which:

Figure 1:
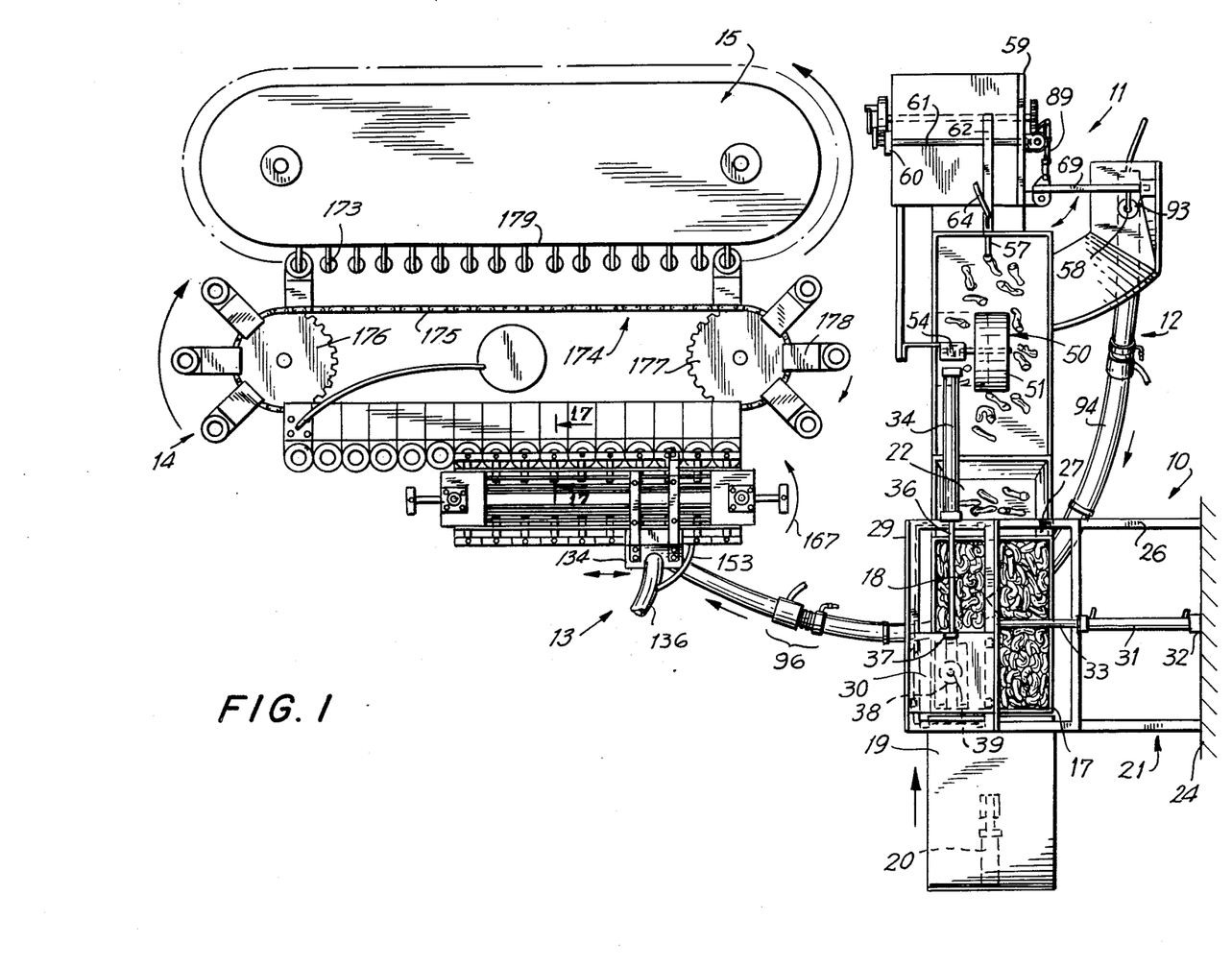
FIG. 1 is a plan view of an apparatus in accordance with the invention.

Referring now to the drawings, there is shown in FIG. 1 a plan view of the entire assembly. The device may generally be described as incorporating separate sections or areas for performing various of the functions required in the mounting of the articles, namely, a bulk supply section 10 which functions to accumulate articles previously manufactured and deposit the same in a single layer; a singulator mechanism 11 adapted to pick up individual said articles and deposit the same in a conduit; conduit assembly 12 for receiving the individual articles and orienting them; cleaning them, and transferring the same to a first loading apparatus 13, the apparatus 13 functioning to position the articles in vacuum chamber assemblies 14 wherein the articles are distended and mounted on mandrels for further processing in the testing zone 15.

BULK SUPPLY SECTION

Referring first to section 10 of the apparatus, the essence of which is best perceived for a consideration of FIGS. 1 to 5, there is provided a floor standing frame assembly 16 on which is mounted a supply box 17, the box having been loaded with a multiplicity of condoms or like articles 18. For purposes which will appear hereinafter, there may be provided a slide chute 19. Preferably the chute 19 is supported at the end of a hydraulic or pneumatic motor mechanism 20 which is shiftable in a horizontal plane into covering and uncovering position of the open top 17a of the box 17.

Referring now to FIGS. 2 to 5, there is shown at 21 an overhead pickup mechanism, the purpose of which is to extract a limited number of articles from the supply box 17 and deposit them on the inclined feeder tray 22 leading to the singulator apparatus 11. The pickup mechanism 21, which is preferably mounted on its own frame assembly 23 made fast to a wall or bulkhead 24, includes a spaced pair of parallel rails 25, 26, on which rails a shuttle frame 27 is slidably mounted.

The shuttle frame 27 in turn carries a pair of parallel walls 28, 29 which are aligned perpendicular to the rails 25, 26. Carriage member 30 is mounted for sliding movement along the rails 28, 29. As will be most clearly apparent from an inspection of FIG. 2, the carriage member 30 is movable toward and away from the bulkhead 24 as well as longitudinally in a direction parallel with the bulkhead, the first noted movement being provided by a sliding of the shuttle from 27 on rails 25, 26, and the second movement being accomodated by a relative movement of the carriage 30 along rails 28, 29.

Figure 2:
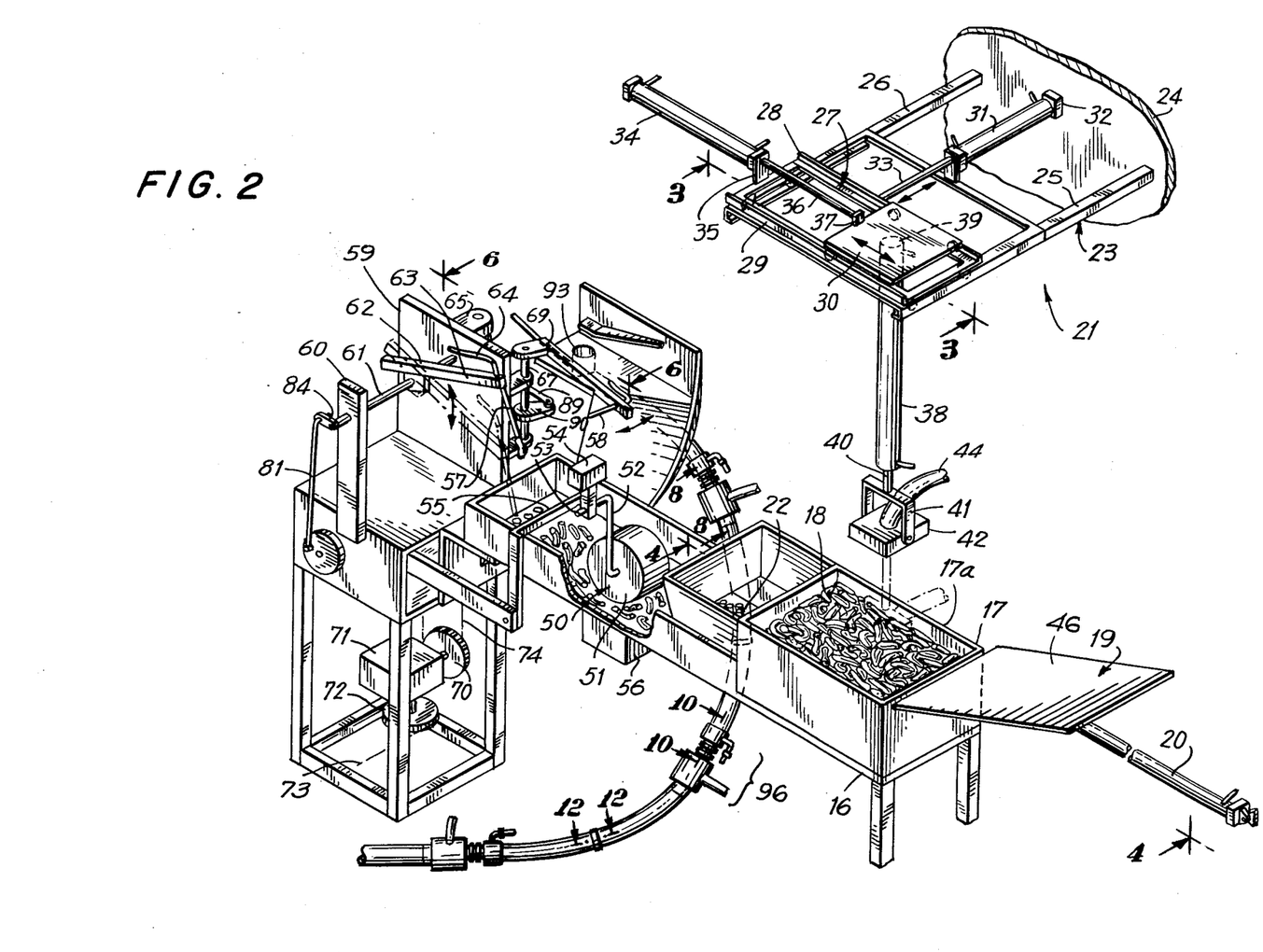
FIG. 2 is a perspective view of the article supply assembly portion of the apparatus.

Movements in the desired directions are powered by first and second double acting piston and cylinder assemblies or motor assemblies 31 and 34 respectively. The assembly 31 includes and end 32 which is fixed to the bulkhead, the piston rod 33 of assembly 31 being secured to the shuttle 27. It will be apparent that the extension or retraction of the motor means 31 will govern the spacing of the shuttle from the bulkhead 24.

In similar fashion, the second linear acting pneumatic cylinder and piston assembly or motor assembly 34, has an end 35 fixed to the shuttle 27 and includes an extensible piston rod 36 fixed at 37 to the carriage 30, whereby the carriage 30 may be shifted in the direction parallel to the bulkhead in accordance with the extended position of the piston rod 36.

A lift cylinder assembly 38 has its upper end 39 secured to the underface of the carriage 30. The cylinder assembly 38 includes a downwardly directed piston rod 40 carrying yoke 41, the yoke 41 in turn providing a support for a suction pickup member 42.

Figure 4:
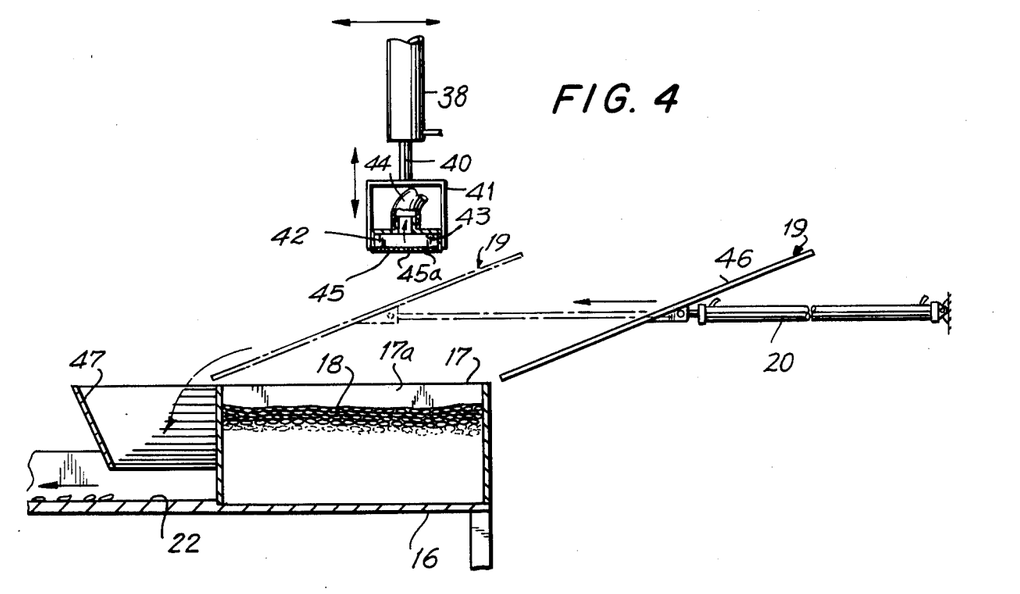
FIG. 4 is a magnified fragmentary vertical section taken on line 4—4 of FIG. 2.

As will be apparent from an inspection of FIG. 4, the suction pickup head 42 includes a hollow chamber 43 connected via conduit 44 to a vacuum source. The undersurface of the head 42 includes a perforate plate 45, the plate embodying a limited number of spaced-apart downwardly directed apertures, e.g., 45a.

Figure 5:
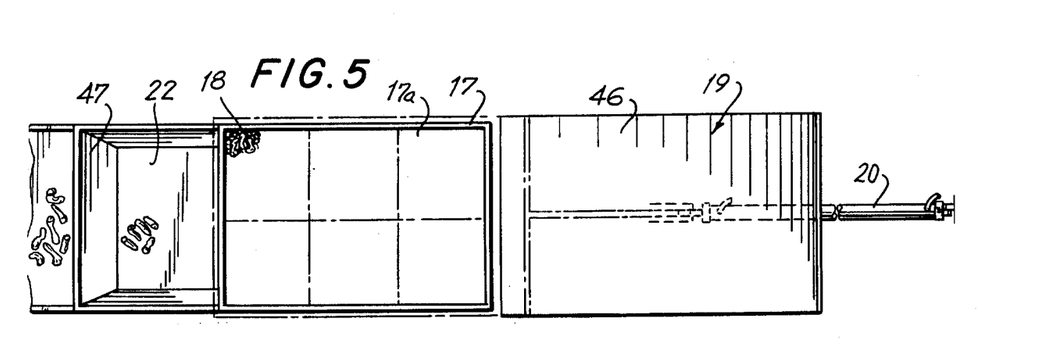
FIG. 5 is a plan view of the article bulk storage components of the apparatus.

An operative cycle of the bulk supply section 10 includes an actuation of the cylinders 31 and 34 in such manner as to locate the suction pickup 41 over the supply box in one of six selected positions, shown in dash lines, FIG. 5.

Selection of the specific area may be manually effected by appropriate control mechanism or the apparatus may be set periodically to align the suction head sequentially in the six positions, or sensing mechanism may be employed to detect the areas of maximum concentration within the supply box 17. The appropriately positioned suction head 42 is then caused to be lowered by energization of the lift assembly 38, whereby the perforate plate 45 is pressed against or adjacent articles in the supply box 17.

Due to the sub-atmospheric pressure existing within the manifold 43, a number of articles 18 are drawn and retained against the apertures 45a in the plate 45. Accordingly, when the lift assembly 38 is energized in an upward direction to withdraw the piston rod 40 thereof, a number of articles are drawn clear of the supply box.

With the pickup head 42 in raised position, as shown in FIG. 4, slide chute 19 is extended into covering relation of the supply box 17 by energization of the cylinder assembly 20, extending the slide chute from the slide to the dot and dash positions illustrated in FIG. 4. Conduit 44 may then be disconnected from the vacuum source, whereupon the articles 18 carried on the undersurface of the plate 45 will fall to the surface of the slide chute, gradually traverse the surface 46 and fall through guide tray 47 to the vibrating feeder tray 22 leading to the singulator apparatus.

Figure 3:
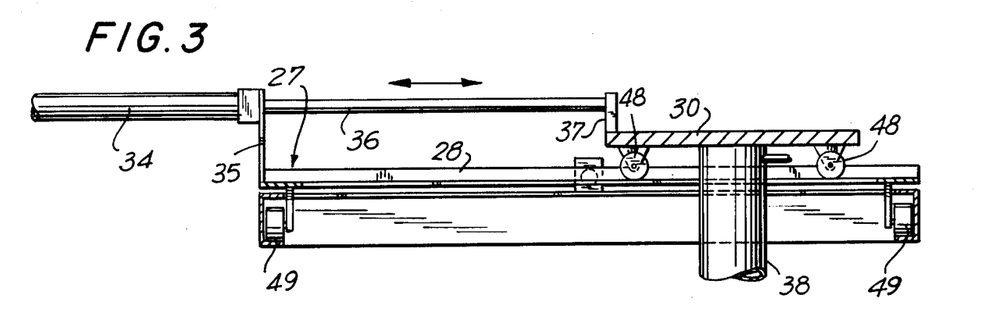
FIG. 3 is a magnified fragmentary vertical section taken on line 3—3 of FIG. 2.

As will be apparent from an inspection in FIG. 3, the carriage 30 may be provided with rollers 48, facilitating traversing the rails 28, 29 and the shuttle 27 may likewise be provided with rollers 49 for traversing rails 25, 26. Additionally, all of the described movements of the carriage, suction pickup and slide chute may be effected responsive to manual or automatic triggering mechanism of essentially conventional design and forming no part of the present invention. Preferably, however, automatic switching mechanism is provided for sensing the presence on the vibrating tray 22 of a sufficient supply of articles 18. The sensing function noted is provided by a pivotally mounted feeler assembly 50.

The feeler assembly 50 includes a roller 51 rotatably mounted on a hanger bar 52, the bar including an inturned end portion 53 supported adjacent a control switch 54. The switch and bar are supported on a bracket arm 55 inwardly extending from the frame. The feeler assembly 50 is pivotally supported by the hanger bar 52 so as to be movable toward and away from the vibrating tray 22.

The tray 22 is slightly inclined toward the singulator 11. A vibrator member 56 is fixed to the tray 22 and the vibrations imparted by the vibrator to the tray cause articles on the tray to advance along the tray in a direction from the supply box to the singulator.

The switch mechanism 54 is so connected as to remain in an "Off" position when the roller 51 is lifted from the tray 22 by the presence of articles 18 between the undersurface of the roller and the top surface of the tray. When there is a shortage of articles, the roller 51 will pivot downwardly toward the tray 22, closing the contacts of the switch 54 and energizing the pickup assembly and slide chute into a depositing cycle, as previously described, whereby additional quantities of articles are removed from the bulk supply and deposited on the tray 22.

SINGULATOR MECHANISM

There will next be described the singulator mechanism, the function of which is to select one and only one article at a time from the tray 22 and deposit the single selected article into the conduit or transfer mechanism 12.

Broadly stated, the singulator mechanism comprises a pair of independent vacuum fingers 57, 58 moving in synchronized relationship, the first mentioned finger 57 picking up a single article from the tray 22, the second finger 58 accepting the article from the finger 57 and depositing the same in the entrance of the conduit or transfer mechanism 12.

It is imperative that only a single article at any given time be dropped into the conduit. The apparatus of the singulator mechanism effects this desired end by providing a single point in space at which the vacuum fingers 57, 58 meet. In this manner, there were, by some mischance, two articles held by the lifting vacuum finger 57, then the second vacuum finger 58 would engage and accept only one of the two, whereby the possibility of two articles being deposited is greatly reduced as the result of the transfer from one finger to another.

More specifically, and with reference particularly to FIGS. 1, 2, 6 and 7, the frame 16 is provided with a vertical plate 59 and a spaced, parallel upstanding bracket 60. A horizontal rocker shaft 61 is journalled between plate 59 and bracket 60 for pivotal movement about a horizontal axis.

Figure 6:
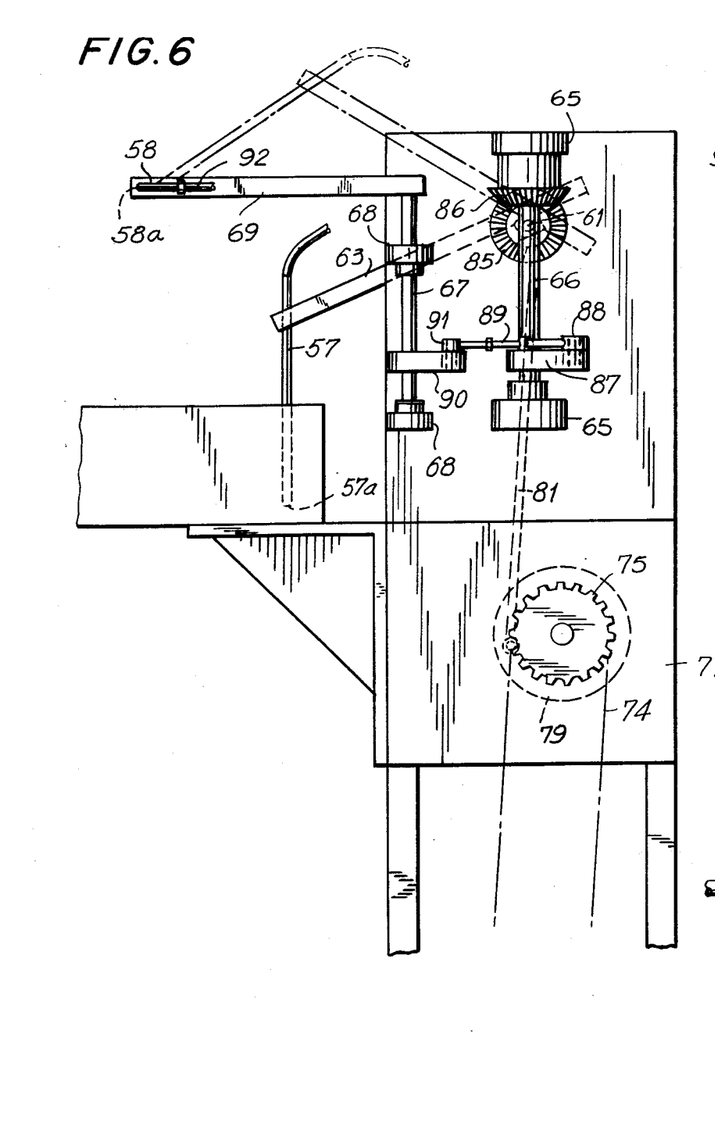
FIG. 6 is a magnified section taken on line 6—6 of FIG. 2.
Figures 7, 7A:
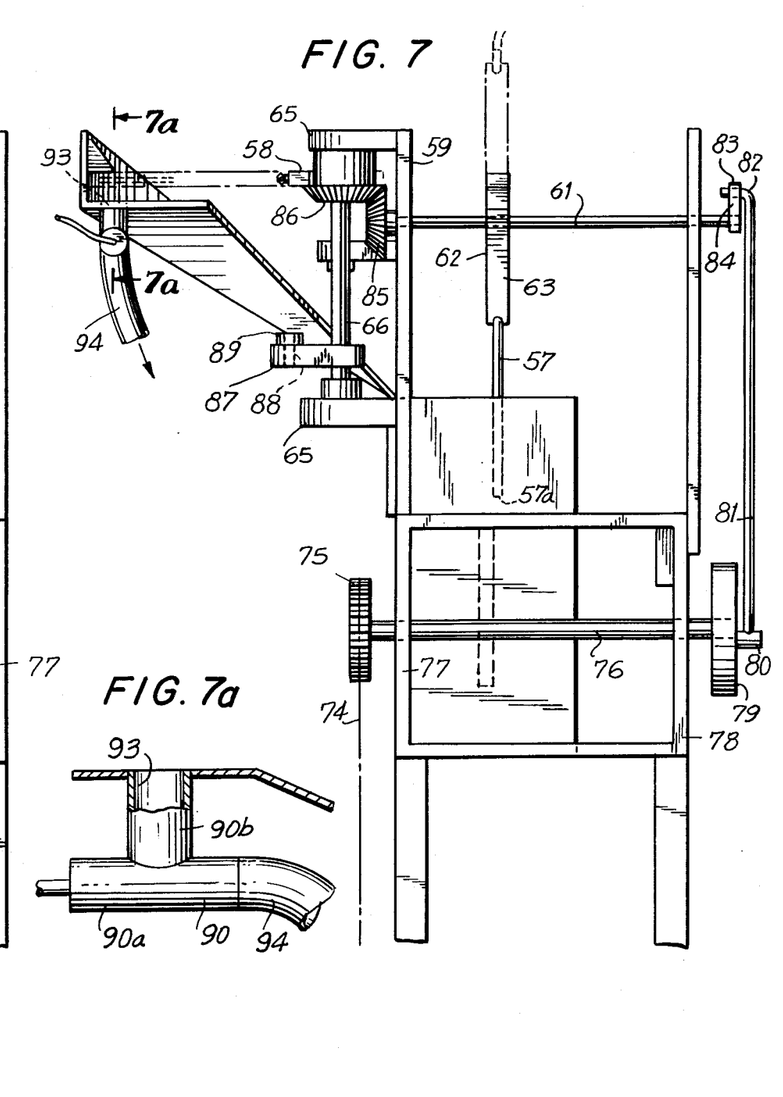
FIG. 7 is a side elevational view of the apparatus of FIG. 6.
FIG. 7a is a detail sectional view taken along the line 7a—7a of FIG. 7.

A rocker arm 62 is made fast at one end to the cross or rocker shaft 61, and arm 62 carrying adjacent its other end 63, the suction finger 57, the finger 57 being hollow and having an outwardly open suction nozzle at its lowermost end 57a. Suction finger 57 is connected to a vacuum source by a vacuum tube 64.

Plate 59 carries a spaced pair of vertically aligned bracket members 65, 65, between which members is journalled a vertical shaft 66. A second vertical shaft 67 is journalled in parallel spaced relation to the shaft 66 within vertical ears 68, 68, welded or otherwise affixed to the plate 59.

Vacuum finger 58 is fixed to an arm 69 secured to the shaft 67. Motive power for shifting the vacuum fingers 57 and 58 in oscillating fashion is provided by a chain drive wheel 70 connected to a gear box 71 which, in turn, is driven from the drive sprocket 72 connected by chain 73 to the drive of the conveyer. A chain 74 (see FIG. 7) meshes with sprocket 75 connected to horizontal cross shaft 76 journalled in side plates 77, 78. The shaft 76 carries a drive disc 79 having a pin 80 eccentrically and rotatably mounted in the disc 79.

A push rod 81 extends upwardly from the pin 80, the rod 81 including an inturned end portion 82 which is pivotally received within an aperture 83 in a link 84 fixed to the outermost end of the cross shaft 61.

From the above described construction it will be evident that motive power supplied by the chain 74 will rotate sprocket 75 and shaft 76 carrying disc 79. Eccentric 80 on the disc will move the lower end of push 81 in an orbital path, causing the cross shaft 61 to pivot in reciprocal fashion first in one direction and then in the opposite direction.

It will further be evident that the arm 62 carrying vacuum finger 57 will be oscillated downwardly and upwardly, bringing the pickup tip portion 57a of the finger 57 cyclically into proximity with the tray 22 and then lifting the tip upwardly from the tray.

Crpss shaft 61 carries at its inner end a bevel gear 85. The bevel gear 85 meshes with a complemental bevel gear 86 made fast to vertical shaft 66. A drive link 87 is made fast to the shaft 66, the link including an upstanding pin 88 on which is pivotally mounted horizontally extending drive bar 89.

The drive bar 89 connects link 87 to a complementary link 90 made fast to the shaft 67 carrying the arm 69 on which is mounted the horizontally shifting pickup finger 58. The bar 89 is fixed to a pin 91 secured rotatably to the link 90 adjacent and end thereof.

From the above described arrangement, it will be appreciated that the back and forth pivotal movement imparted to the cross shaft 61 is communicated through the meshing of the bevel gears 85 and 86 to the vertical shaft 66, whereby the shaft 66 is rotated about a vertical axis through an arcuate movement. Arcuate movement of the shaft 66 is communicated to the shaft 67 through the draw bar 89 connecting links 87 and 90. The vacuum pickup finger 58 which is supported on arm 69 will thus describe a horizontal arcuate path.

The movement of the pickup fingers 57 and 58 is is coordinated that at one point in their cycle when the finger 57 is spaced from the tray 22, the nozzle portion 57a of the finger 57 is disposed immediately adjacent the nozzle 58a of the finger 58.

A conduit 92 is connected to the finger 58. The conduit 92, like the conduit 64 of the finger 57, is connected through an appropriate automatic valving mechanism to a source of vacuum.

The operation of the singulator mechanism will be appreciated from the preceding discription. As noted, the pickup finger 57, the nozzle 57a of which is under suction, is lowered toward the tray 22. An article beneath the tip 57a will be shifted into contact with the tip and when the tip is moved away from the tray, the article will be carried along with the tip. In the meantime, the finger 58 is shifting in a horizontal plane toward the transfer position at which the tips 57a and 58a are disposed in close adjacency.

At the point of close adjacency, vacuum in the line 64 connected to the finger 57 is shut off and air puff is delivered by an appropriate valving mechanism synchronized with the movement of the fingers to release the associated article, the same mechanism placing the conduit 92 connected to finger 58 under vacuum. If a single article has been lifted from the tray 22 by a finger 57, the single article will be released from finger 57 by interruption of the vacuum and an air puff and come under the control of finger 58 by the introduction of vacuum in the line 92.

Continuing movement of the mechanism involves a return or downward movement of the finger 57 toward the tray 22 and a horizontal arcuate movement of the finger 57 toward the entrace 93 to the conduit assembly 12 of the apparatus.

If by some mischance the finger 57 should have been disposed at a position over the tray 22 precisely between two articles resting on the tray in such manner that both said articles have been carried upwardly by the finger 57, it will be evident that one of the two articles, upon relief of the vacuum in conduit 64, will be released and fall back to the tray and the other only will become attached to finger 58.

By effecting a transfer from one vacuum finger to another vacuum finger at a selected point in space, the possibility of depositing two articles at one into the conduit entrance 93 is virtually eliminated.

CONDUIT ASSEMBLY

Articles deposited at the conduit entrance 93 are, as noted, unrolled. Additionally, the formed articles incorporate substantial quantities of talc or dry powdered lubricant on their inner and outer surfaces.

Accordingly, it is a function of the conduit assembly 12 to transport the articles rapidly to mounting position, to orient the articles, and to remove, in large degree, the residue of talc or like powdered lubricant from both the interior and the exterior surfaces of the articles.

Referring now particularly to FIGS. 1, 2 and 8 to 12, it will be seen that the conduit 12 comprises an elongated transfer tube 94 which may be formed or rubber or vinyl, where flexibility is desired, or of metallic material where flexibility is unimportant. Air flow is induced in the conduit by a source of air under pressure which flows into one end of the horizontal leg 90a of a T-fitting 90, to other end being connected to tube 94. The opening or entrances end 93 is defined by the free end of the horizontal leg 90b of the T-fitting, and the article will be drawn by the venturi action into opening 93 and advance toward the exit end 95. The concept of employing a suction conduit or conveyer for the transportation of condoms or like articles is not new per se, forms of such apparatuses being shown in U.S. Pats. Nos. 2,109,150 and 3,253,719.

In accordance with the present conduit construction, there is provided along the length of the conduit a series of accelerator and cleansing stations, such as station 96. The accelerator stations generally comprise a casing 97 (see FIG. 10) including a reduced diameter neck portion 98, over which is sleeved a section 99 of the flexible conduit. The casing includes an annular pressure chamber 100 defined by a pair of radially outwardly directed flanges 101, 102, the flanges being sealed by a circumferential cylindrical closure 103. A plurality of inclined jet apertures 104 are drilled in the casing, the bores or apertures 104 including radially inwardly directed components as well as components aligned with the direction of movement of the articles traversing the conduit. The chamber 100 is connected via nipple 105 to a source of air under pressure. A baffle portion 106 is formed in the casing immediately upstream of the exit end portions or the jets 104.

Figures 8, 9, 10:
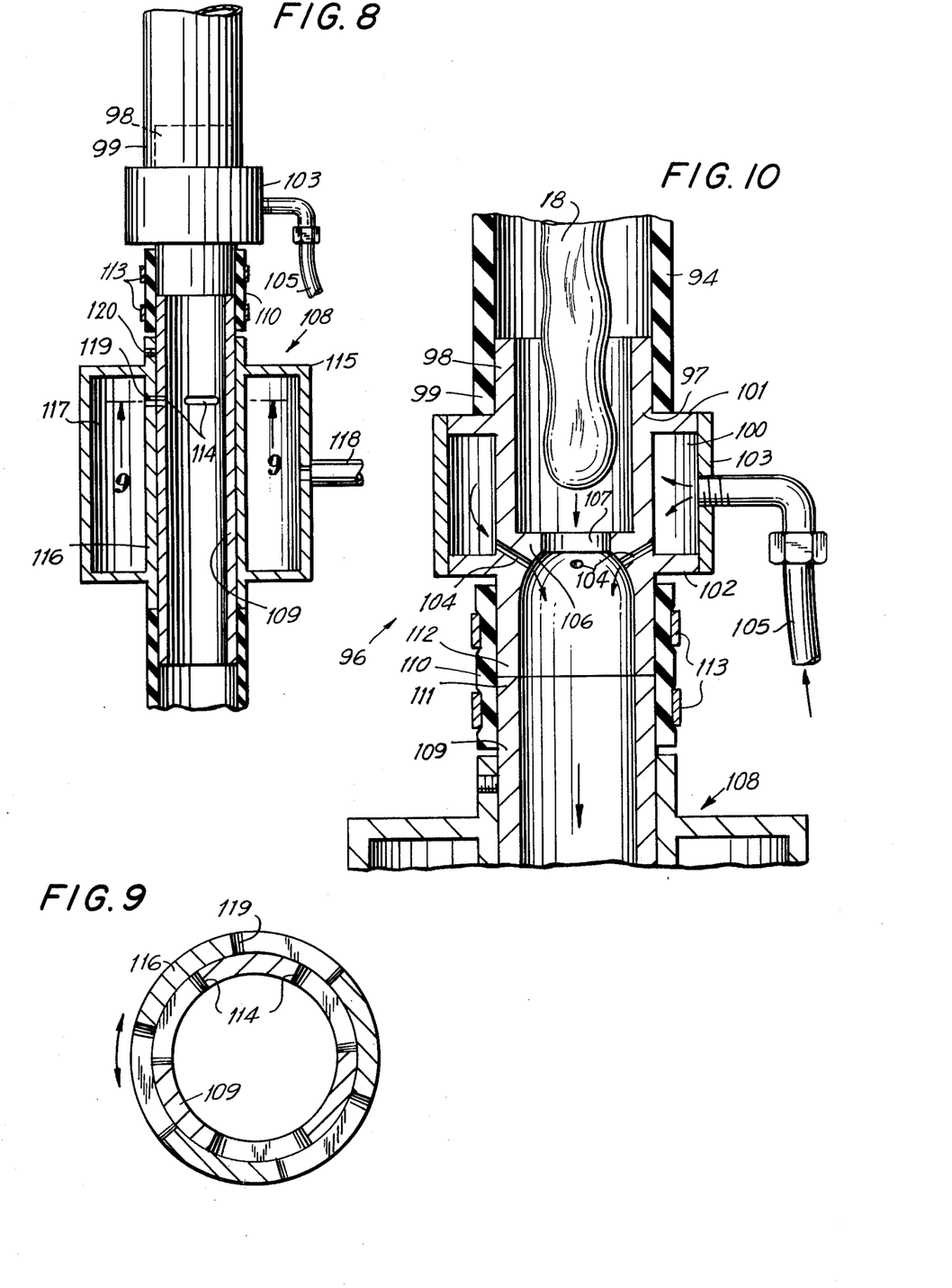
FIG. 8 is a magnified section taken on line 8—8 of FIG. 2.
FIG. 9 is a magnified horizontal section taken on line 9—9 of FIG. 8.
FIG. 10 is a magnified section taken on line 10—10 of FIG. 2.

As will be observed from an inspection of FIG. 10, articles traversing the conduit 94 and entering the casing area will be deformed upon passing through the restricted aperture 107 of the baffle 106. The articles will be urged into a relatively radially compressed condition not only by the restricted size of the aperture 107 but also by the inward force components exerted on the article by the converging jets 104.

Additionally, since the jets incorporate force components aligned with the direction of movement of the articles, the jets tend to accelerate the articles in their intended direction of movement.

A further function of the baffles 106 is to induce an orienting of the articles, the orienting influence being the result of the tendency of the thickened rim of the articles to spread radially and thus exert a drag, particularly as the article is pulled through the baffle areas 106, with the rim thereof engaging the periphery of opening 107.

Immediately downstream of each pressure casing 97 is a vacuum casing assembly 108. The vacuum casing assembly includes an inner sleeve portion 109. A sealing sleeve 110 laps the junction between the lead end 111 of the sleeve 109 and the trailing portion 112 of the casing 97. Preferably annular clamps 113 maintain the sealing sleeve in the position noted. The sleeve 109 is provided with a series of arcuate slot-like apertures 114 extending radially outwardly through the walls thereof. A vacuum canister 115 is mounted over the sleeve 109 and is rotatable relative thereto. The vacuum canister includes a cylindrical inner wall 116, the wall 116 forming the innermost boundary of an annular vacuum chamber 117 connected via vacuum hose 118 to a vacuum pump.

The wall 116 includes a plurality of arcuate slots 119 which may be rotated into registry with the slots 114 or partially out of registry with the noted slots and locked in the desired position by set screw 120. By relative rotation of the canister 115 and sleeve 109, the effective passageway provided from the vacuum canister through slots 119 and 114 to the interior of the conduit 94 may be adjustably controlled (see FIG. 9).

It will be observed from a inspection of FIG. 8, for example, that a negative pressure is maintained in the conduit upstream of the canister 115 by the outflow of air into the conduit 118. As the canister is positioned immediately downstream of barrier 106 a substantial quantity of talc will be dislodged from the exterior surface of the article at a position just upstream of the vacuum canister, whereby talc, etc. is drawn outwardly through conduit 118. Since the articles passing beyond the apertures 114 are moving at a substantial rate of speed, there is no significant tendency for the articles to become attached to the apertures under the negative pressure influences existing within the canister.

It will be appreciated that one or more combined pressure and vacuum stations may be employed in accordance with the characteristics of a particular installation, i.e., length of conduit, etc. Three such stations are shown in the illustrated embodiment.

Figure 11:
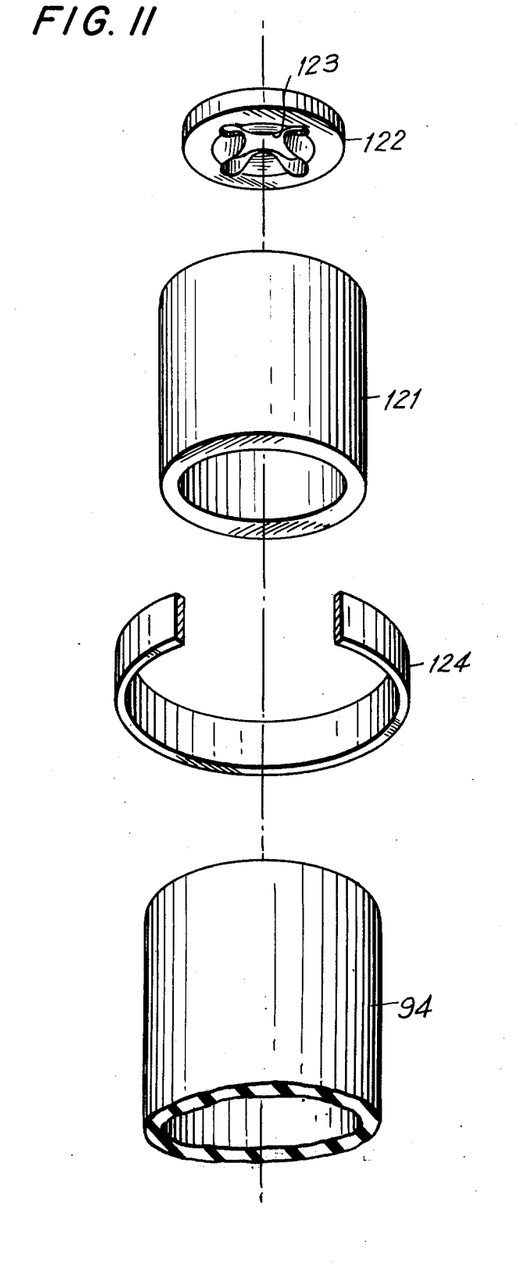
FIG. 11 is an exploded isometric view of a baffle component of the conduit system for transferring individual articles from a bulk supply to the mounting mechanism.
Figure 12:
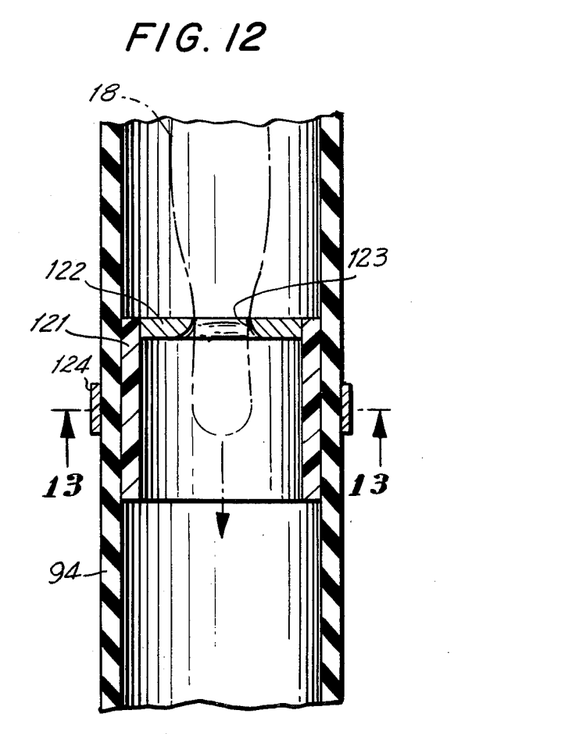
FIG. 12 is a section taken on line 12—12 of FIG. 2.
Figure 13:
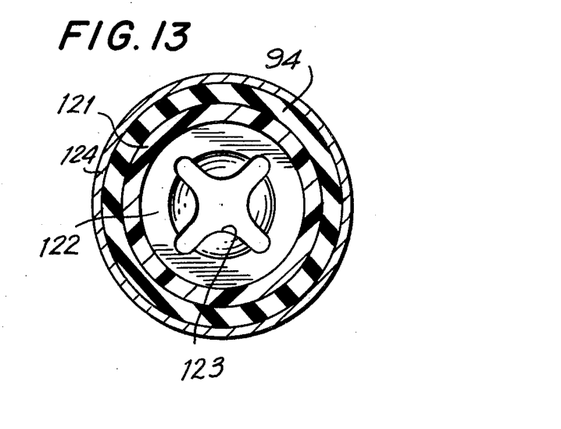
FIG. 13 is a horizontal section taken on line 13—13 of FIG. 12.

In addition, and in order to assure full orienting of the articles, one or more barrier stations of the type illustrated in detail in FIGS. 11 to 13 may be interposed along the length of the conduit. The barrier stations may consist simply of an insert sleeve 121, the outside diameter of which closely nests with the inside diameter of the conduit 94. A baffle member 122 may be disposed in tightly wedged engagement within the insert sleeve 121. Optionally the aperture 123 formed in the barrier may be cruciform in transverse section. A spring clamp member 124 may be lapped about the conduit 94 in registry with the sleeve 121, locking the parts together against downstream movement.

From the foregoing description of the conduit assembly it will be observed that as a result of the combined pressure and vacuum stations and restricting barriers described, the articles traversing the conduit will have been oriented, with their closed end forward and have their external surfaces essentially cleared of talc. It will be further appreciated that the treatment steps in the conduit have done little to remove such talc or like residue as may exist in the interior of the articles.

In accordance with the present invention, the interior surface of the article descending the conduit is cleaned by causing the articles which are moving rapidly, closed end first, toward the exit station 95 to become everted over the intermediate of carrier mandrels 125.

Carrier mandrels 125, which will be described in greater detail hereinafter, are vertically arrayed and include a depending tip 126. The upper end portions 127 of the carrier mandrels 125 are connected to offset links 128 secured to a horizontally arrayed chain flight 129.

Figure 16:
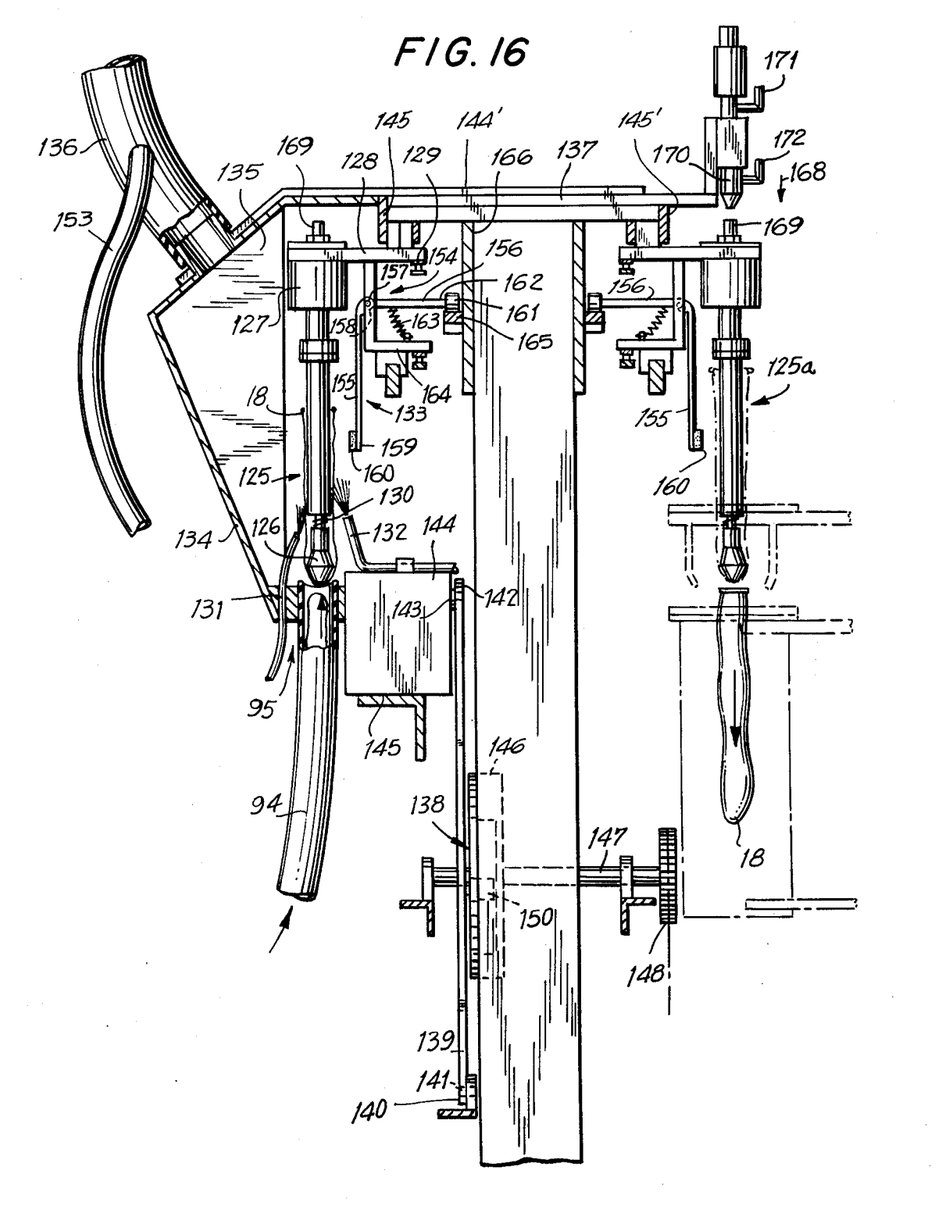
FIG. 16 is a section taken on line 16—16 of FIG. 14.

Referring particularly to FIG. 16, the chain 129 which carries a series of mandrels 125 progressively aligns the mandrels with the exit end 95 of the conduit. The vacuum and pressure components of the stations 96 are adjusted in such manner that the articles are advancing at a speed sufficient to permit the same to evert when impacted, closed end first, against the lower end of the tips 126 of the mandrels 125.

Preferably, the tip 126 of the mandrel is movable in a vertical direction relative to the main body of the carrier mandrels, the movement being resisted by springs 130, whereby the shock resulting from impact is somewhat reduced, and a clamping action takes place while vacuum is drawn.

As a result of the noted eversion, it will be apparent that the talc covered interior portions of the articles now form the exterior portions, exposing the same for removal of excess talc, etc. A pair of pressure jets 131, 132 are disposed adjacent the exit end 95 of the conduit. The jets 131, 132 function to force air against the newly exposed sides of the article, the blasts dislodging adherent talc components and also serving to retain the articles in position on the carrier mandrels until the same come under the control of clamp mechanism 133, the operation of which is next to be described.

INTERMEDIATE CONVEYER

In advance of the description of the intermediate conveyer, it should be noted that the exit station 95 is partially surrounded by a movable vacuum hood assembly 134, including vacuum manifold 135 connected by conduit 136 to a vacuum pump, whereby the excess talc blasted clear of the exposed surfaces of the articles by jets 131, 132 is drawn away from the apparatus.

The manifold 135 overlies the transition area 137 wherein the articles are transferred from the conveyer 94 to the mandrels 125. The air blast jets 131, 132 are mounted for reciprocal movement in such manner that the same will advance along with an article newly mounted on a mandrel 125 to maintain the article on the mandrel and clear the surface of the article of talc.

Reciprocal movement of the jets 131, 132 and manifold 135 is effected by a drive assembly 138, including a driver lever 139 pivoted at its lower end 140 on a pivot pin 141 affixed to the frame. The upper end 142 of the lever carries a pin 143 pivotally secured to carriage 144 and cross struts 144' which are slidably mounted for reciprocal movement along rail sections 145 and 145' respectively. A drive wheel 146 is fixed to drive shaft 147 carrying sprocket 148 driven by a power takeoff from the main drive for the conveyer mechanism.

Drive wheel 146 includes an eccentric cam track 149. A follower pin 150 is fixed to the lever 139, the innermost end 151 of the lever riding within the cam track 149, whereby it will be appreciated that a rotation of the wheel will produce a back and forth movement of the carriage 144, manifold 135 and jets 131, 132.

The carriage 144 is timed to move in synchronism with the mandrels 125 advancing in the direction of arrow 151 (FIG. 14) in such manner that the carriage and air blasts are aligned with the discharge exit end 95 of the conduit 94 when a mandrel passes over the exit end of the conduit, the carriage thereafter moving downstream with the mandrel for at least the first few inches of its movement.

A vacuum manifold 152 likewise is mounted on the carriage, the manifold being connected to the main vacuum source 136 by a vacuum takeoff conduit 153.

Clamp mechanism 133 functions mechanically to engage articles mounted on the mandrels 125 as the same move away from the exit 95 and maintain the same in position on the mandrels as the articles pass beyond the influence of the air blasts.

Each clamp mechanism 133 includes a generally L-shaped lever 154 including a depending vertical arm 155 and a horizontal arm 156. The levers 154 are pivoted at 157 to brackets 158 depending from conveyer links 128. The end 159 of arm 155 includes a sponge pressure pad 160. A follower roller 161 is mounted on the end 162 of arm 156 of the clamp. A tension spring 163 is biased between arm 156 of lever 154 and base 164 of bracket 158.

It will thus be observed that the tension of the spring will tend to urge the arm 156 of the lever in a downward direction, inducing a clockwise pivotal movement of the lever when viewed in the orientation of FIG. 16, which clockwise movement would bring the pressure pad 160 into engagement with an article mounted on carrier mandrel 125.

A fixed cam track 165 is mounted on a stationary frame portion 166, the track is disposed below the roller 161, the latter being held against the track by spring 163. It will be observed that when the track is at a height such as illustrated in FIG. 16, the roller 161 will be lifted, causing the clamp mechanism to be rotated in an anti-clockwise direction, whereby the pressure pad is cleared from the article. Conversely, when the track is disposed at a lower level the spring 163 is permitted to rotate the lever clockwisely and shift the pressure pad 160 into clamping position toward the mandrel (FIG. 14).

Figure 14:
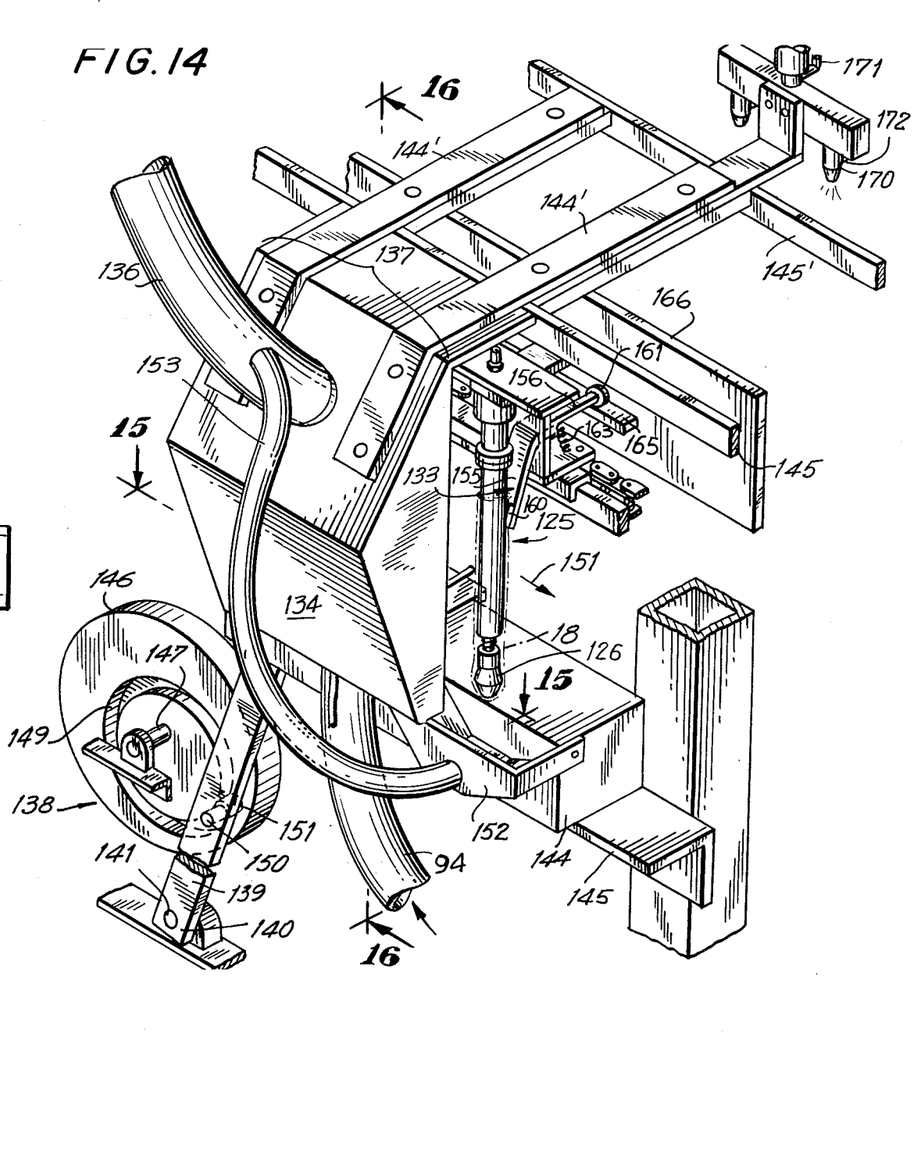
FIG. 14 is a perspective view on an enlarged scale of a portion of the mounting mechanism.
Figure 15:
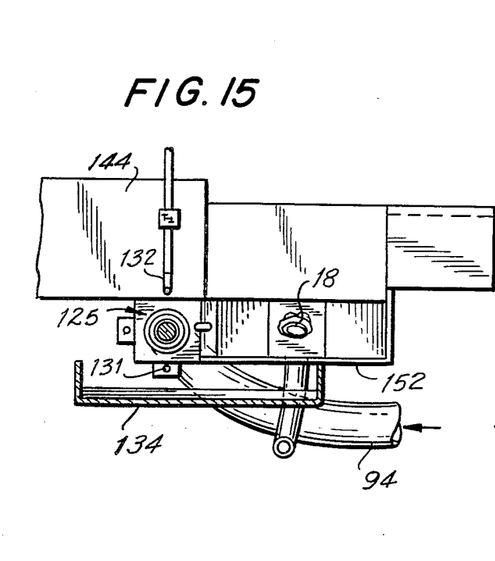
FIG. 15 is a horizontal section taken on line 15—15 of FIG. 14.

As best appears from FIGS. 1, 14 and 16, the articles, after mounting on the mandrels 125, will be supported by the pressure pads 160 and moved in the direction of arrow 167 (see FIG 1) to a station whereat the articles are introduced into vacuum chambers where they are distended as a result of subjecting the exterior to a subatmospheric pressures while the interior is maintained at atmospheric pressure. Testing mandrels may then be inserted into the articles without fear of tearing the articles.

As seen in FIG. 16, mandrel 125a has reached discharge station 168. At such station, the level of the cam track 165 is raised, as contrasted with the level of the track in the area leaving the mounting station, whereby the arm 156 of the lever will be pivoted to a height sufficient to release the article which had previously been sandwiched between the mandrel 125a and pressure pad 160.

In order to assure positive discharge of the articles, the mandrels 125 are provided with elongated hollow cores 169 running the entire length of the mandrels, terminating at the tips 126 thereof.

The movable carriage 137 carries one or more air discharge jets 170, the jets being operatively connected via conduits 171, 172 to emit a puff of air when the article is in registry above the vacuum receiver mechanism to aid in dislodging of the article from the intermediate conveyer.

VACUUM MOUNTING MEANS

The vacuum mounting means which functions to rereceive the discharged articles and mount the same on enlarged test mandrels 173 in essentially the form illustrated, is described in U.S. Pat. No. 3,588,997 and, accordingly, a detailed explanation of the operation thereof need not be supplied. It is sufficient to an understanding of the present invention to note that 174 represents a vacuum mounting conveyer including chain flight 175 stretched between two spaced sprockets 176, 177. A plurality of offset link arms 178 carry vacuum chambers and associated apparatus for fully distending the deposited articles which, after distension, are sleeved over and mounted on test mandrels 173 carried by test conveyer 179.

Referring particularly to FIGS. 17 to 19, 180 represents an open ended container which may, through appropriate valving, be connected via conduit 181 to a vacuum pump. At 182 there is shown a pair of clamp jaws provided on their undersurface with a rubber gasket 183 in airtight relation to the upper face 184 of the vacuum chamber. The jaws, when moved together, define therebetween a relatively small opening 185 through which the body of the article may pass, but not the rim portion R.

Figure 17:
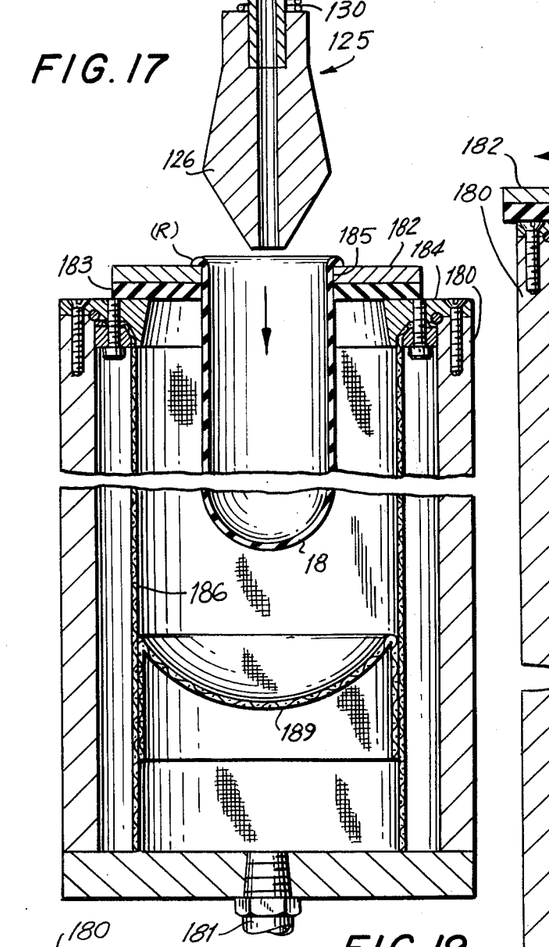
FIG. 17 is a fragmentary vertical section through a vacuum chamber depicting the parts in position for loading.

As shown in FIG. 17, the article is released so that the major part thereof extends into the vacuum chamber 180, the rim R being suspended in the aperture 185 in the jaws 182 and clamped by a spring loaded prong. Partial vacuum is then drawn in the container 180, causing the article to expand and line an internal screen portion 186 formed inside of the container 180 in spaced relation to the walls thereof. The jaws 182 are then opened from the position shown in FIG. 17 to that of FIG. 18, whereupon the major body portion of the article will line the screen but the rim R and the areas of the article immediately adjacent the rim will droop to one of the positions shown in dot-and-dash lines in FIG. 18.

Figure 18:
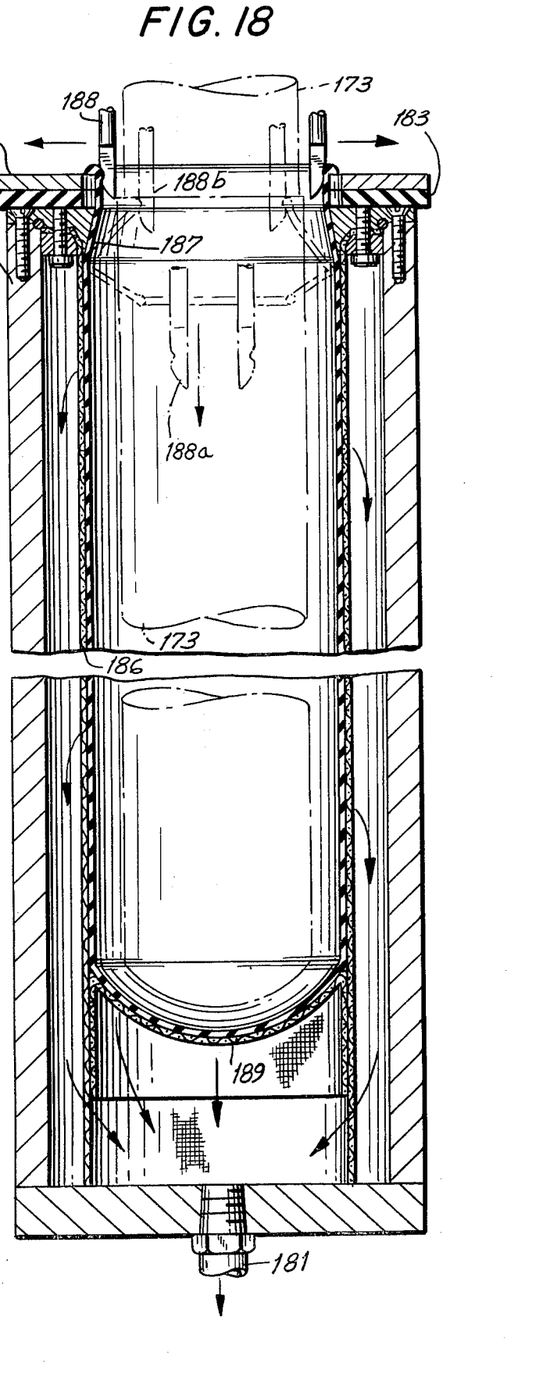
FIG. 18 is a vertical section through the vacuum chamber showing the article stretched within the vacuum chamber.

It is to be noted that the vacuum is not broken upon opening of the jaws 182 since the seal between the article and a solid portion of the container is formed in the annular area 187.

It is now necessary to stretch or open the neck portion to permit passage of the test mandrels 173, the diameter of which is larger than the diameter of the undistended rim. For this purpose there is provided a series of mechanically operated spreader fingers 188 which are introduced into the article through the rim end thereof, with the fingers in close spaced relationship, as shown at 188a—dash lines, FIG. 18, the fingers being progressively spread and moved outwardly through the mouth opening to pick up the rim of the article, as shown at 188b, the final or fully spread position of the rim being shown in solid lines in FIG. 18.

As is apparent from FIG. 18, the entirety of the article is now distended by the combination of spreading effected by fingers 188 and the vacuum to a dimension in which test mandrels 173 may be freely inserted into the interior thereof without chafing or rubbing contact with the articles.

As noted in U.S. Pat. No. 3,588,977, insertion of the mandrels 173 into the stretched articles is effected by a relative movement of the vacuum canisters and test mandrels, i.e., either downward movement of the mandrels or upward movement of the canisters or chambers. When the mandrels are entirely inserted into the distended articles — see dot-and-dash position, FIG. 18 — vacuum is relieved, whereupon the elasticity of the articles will cause them to shrink and intimately conform with the mandrel.

It will be appreciated that the mandrels, mounted on the conveyor 179 are thereafter shifted outwardly of the containers carrying the articles into an electrical or like testing cycle in the test mechanism 15.

Figure 19:
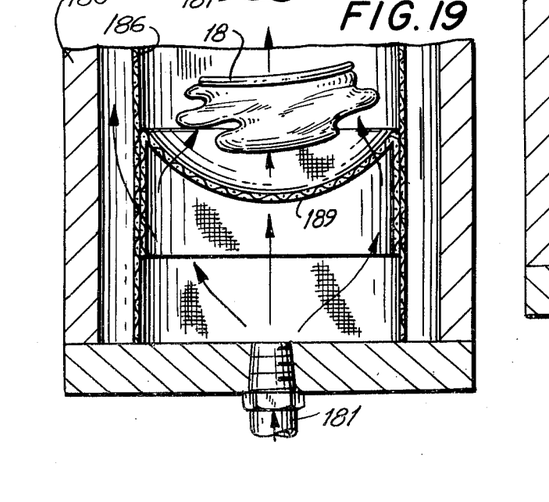
FIG. 19 is a vertical sectional view through the lower portion of the vacuum chamber depicting an article which has become displaced in the course of loading.

Preferably, after the mandrels carrying the articles are withdrawn from the canisters, the conduit 181 is connected to a source of air under pressure and a short burst of air introduced into the bottom of the canister. The burst of air is effective to clear from the canister an article or articles which may have fallen into the interior of the chamber and lie adjacent the floor portion 189 thereof (FIG. 19).

OPERATION

The operation of the device will be evident from the preceding description.

Briefly, articles from the supply box 17 are deposited on the vibrating tray 22. Articles are picked up from the tray by the singulator finger 57 which, in the manner noted, lifts from the tray, an article disposed beneath the finger and delivers the same to a second singulator finger 58, the fingers meeting in free space once during each cycle of reciprocal operation of the fingers, whereby the possibility of two articles being simultaneously supported on finger 58 is reduced or eliminated.

An article adherent to suction finger 58 is deposited in the entrance 93 of conduit 94. The article is drawn through the conduit by the venturi action caused by the flow of air under pressure through the horizontal leg of the T fitting 90 to which the inlet 93 is connected through the vertical leg of the T fitting, the article passing, in the course of traversing the conduit, beyond a series of baffles, e.g., 122, and accelerator and cleaning stations, e.g., 96.

The articles are oriented and the exposes outer surfaces thereof cleaned of excess quantities of talc. The articles are rapidly advanced, closed end first, into contact with the carrier mandrels 125 and caused to evert as a result of the impact against such carrier mandrels.

Synchronization of the delivery of an article with a carrier mandrel is automatically effected since the singulator and the conveyor for the carrier mandrels operate in timed relation from a common drive source, and the time required for an article to traverse the conveyer is essentially constant for each operating cycle.

The everted articles are cleaned on their newly exposed outer surfaces by air blasts through jets 131 ad 132, and maintained in position on the carrier mandrels 125 by the force of such jets until the gripping function is transferred to the pressure pads 160 of levers 154. The articles are retained by the levers against the mandrels until reaching the discharge station 168, whereat the cam track 165 causes the levers to pivot releasing the article while simultaneously a puff of air is introduced through the tubular core 169, forcing the articles downwardly to the position shown in FIG. 17, whereat the article extends through the aperture 185 formed by the jaws 182, the rim R being seated at the upper end of the aperture and clamped by the nose of prong 126.

Chambers 180 are thereupon subjected to vacuum to distend the article as the result of atmospheric pressure within the articles exceeding subatmospheric pressure within the canisters. After the vacuum is drawn, jaws 182 are moved apart and spreader fingers 188, in a collapsed condition, caused to enter the article through the neck of the article. The fingers 188 are moved apart and simultaneously lifted to expand the rim of the article and to assure that the rim lies outside the article. The fully expanded article is now sleeved over test mandrel 173, the vacuum relieved, at which point the article will be supported under its own elasticity on the test mandrel for subsequent processing in a testing apparatus.

After testing, the articles are unrolled from the mandrels in conventional manner, the rolling being typically effected by inclined brushes which rotate and cause a progressive furling of the articles until the same are released from the mandrels.

From the foregoing it will be apparent that there is defined a novel method and apparatus for mounting elastic articles, such as condoms, on test mandrels. The apparatus and method are particularly characterized by a positive feed and effective control over the articles in all stages of transfer.

The apparatus includes mechanism for assuring that only a single article at a time is processed, and for cleaning both the interior and exterior surfaces of the articles of talc or like dry powdered lubricant and orienting the articles closed end first.

Variations of the method and apparatus will occur to skilled workers in the art in the light of the instant disclosure. Accordingly, the invention is to be broadly construed within the scope of the appended claims.

Having thus described my invention, what I claim as new and desire to secure by Letters Patent Of the United States is:

1. Apparatus for mounting a rimmed open mouth, distensible and inflatable article, such as a condom, on a test mandrel or the like of larger diameter than the undistended condom, comprising in combination, a frame, conveyer means movably mounted on said frame, a plurality of elongated carrier members having a diameter smaller than the diameter of said articles, said carrier members including a first end portion fixed to said conveyer means and a distal end portion spaced from said conveyer means, drive means operatively connected to said conveyer means for moving said conveyer means progressively to advance successive said carrier members to a receiver station, transfer means having an exit end adjacent said receiver station for delivering fully unrolled articles closed end first to said receiver station along a path parallel to the longitudinal axis of said carrier means in timed relation to the movement of said carrier means, whereby the closed end of each successive article reaching said receiver station is impacted against the distal end of successive said carrier means at said station, said articles being advanced by said transfer means at a speed sufficient to evert said articles over said carriers, retainer means cooperating with said carriers for holding said articles in position on said carriers as the latter leave said station under the influence of said conveyer means, and article stretcher means including vacuum chamber for receiving articles from said carrier members expanding the same to a diameter greater than said test mandrels, and mounting the same on said test mandrels.

2. Apparatus in accordance with claim 1 and including retainer means for supporting said everted articles on said carrier members, said retainer means including levers shiftable toward and away from said carrier members, the combination including cam and follower means interposed between said levers and frame for shifting said levers toward and away from said carriers responsive to relative movement of said conveyer and said frame.

3. Apparatus in accordance with claim 2 wherein said cam and follower means include a cam track on said frame, a follower on said levers biased into engagement with said track, said cam and follower means holding said levers away from said carrier members when the same arrive at said receiver station and shift said levers into contact with a said condom to clamp the same against said carrier member when the same depart said receiver station.

4. Apparatus in accordance with claim 1 and including air jet means adjacent said receiver station, said jet means being directed generally toward and longitudinally of said carrier member for clearing detritus from the exterior of said articles, and maintaining said everted articles in position on said carrier members.

5. Apparatus in accordance with claim 1 wherein said transfer means comprises an elongated tube member having a loading station at one end, the other end of said tube member being disposed at said receiver station, means for inducing air flow within said tube member in a direction from said loading station to said receiver station, at least one orienting and accelerator station intermediate said tube, said station including a partial barrier member having portions projecting inwardly from the walls of said tube member to define a restricted passage portion having cross sectional dimensions smaller than the dimensions of said rim portions, and air jet means immediately downstream of said partial barrier members for introducing air under pressure into said tube, said jet means being oriented in a direction to provide force components aligned with the direction of flow of the air in said tube.

6. Apparatus in accordance with claim 5 wherein said air jet means includes a plurality of separate jet members, said jet members being symmetrically, angularly spaced apart about said tube and being equidistant from the longitudinal axis of said tube.

7. Apparatus in accordance with claim 5 and including a pressure relief station in said tube immediately downstream of said accelerator station, said pressure relief station including pressure relief port means formed in the walls of said tube and a vacuum manifold connected to said pressure relief port means.

8. Apparatus in accordance with claim 7 wherein said pressure relief port means comprises a plurality of apertures formed in the walls of said tube, said apertures being disposed in coplanar alignment in a plane normal to the longitudinal axis of said tube, said ports being symmetrically angularly spaced apart, whereby the pressure relief flow through said apertures is symmetrical with respect to said longitudinal axis.

9. Apparatus in accordance with claim 8 and including a rotatable sleeve member covering said apertures and interposed between said apertures and said manifold, said sleeve member including apertures in registry with the apertures in said tube whereby the effective dimension of said pressure relief ports may be varied in accordance with the relatively rotated position of said sleeve and tube.

* * * * *